US012796929B2

(12) United States Patent
White et al.

(10) Patent No.: US 12,796,929 B2
(45) Date of Patent: Nov. 17, 2026

(54) PRESENCE AND VITALS DETECTION OF LIVING SUBJECT USING LWIR AND RADAR SYSTEMS

(71) Applicant: Innovative Health Monitoring LLC, Stamford, CT (US)

(72) Inventors: Eric Gregory White, Tinton Falls, NJ (US); David Robert Abrams, Aberdeen, NJ (US)

(73) Assignee: Innovative Health Monitoring LLC, Stamford, CT (US)

( * ) Notice: Subject to any disclaimer, the term of this patent is extended or adjusted under 35 U.S.C. 154(b) by 142 days.

(21) Appl. No.: 17/872,952

(22) Filed: Jul. 25, 2022

(65) Prior Publication Data

US 2023/0036335 A1 Feb. 2, 2023

Related U.S. Application Data

(60) Provisional application No. 63/226,703, filed on Jul. 28, 2021.

(51) Int. Cl.
*A61B 5/00* (2006.01)
*A61B 5/01* (2006.01)
*A61B 5/05* (2021.01)

(52) U.S. Cl.
CPC ............ *A61B 5/0035* (2013.01); *A61B 5/015* (2013.01); *A61B 5/05* (2013.01); *A61B 2503/04* (2013.01)

(58) Field of Classification Search
None
See application file for complete search history.

(56) References Cited

U.S. PATENT DOCUMENTS

2008/0045847 A1 2/2008 Farag et al.
2008/0119716 A1* 5/2008 Boric-Lubecke .... A61B 5/7225 600/407
2008/0142713 A1 6/2008 Breed et al.
2014/0023235 A1 1/2014 Cennini et al.
2014/0058256 A1 2/2014 De Jong
2014/0071242 A1* 3/2014 Lin ......................... G06T 7/254 348/46
2014/0326888 A1 11/2014 Barlow et al.
2015/0078642 A1 3/2015 Fang
2016/0151603 A1 6/2016 Shouldice et al.
2017/0188938 A1* 7/2017 Toh ......................... H04W 4/38
2017/0303830 A1 10/2017 Klein et al.
(Continued)

OTHER PUBLICATIONS

International Search Report and Written Opinion for PCT Application PCT/US2022/038214, mailed on Oct. 12, 2022.
(Continued)

*Primary Examiner* — Christopher Koharski
*Assistant Examiner* — Farouk A Bruce
(74) *Attorney, Agent, or Firm* — Greenberg Traurig, LLP

(57) ABSTRACT

A method and system for presence and vitals detection of a living subject is disclosed herein. The system comprises a passive long wave infrared ("LWIR") sensor, a radar, a processor and a user interface. The LWIR sensor is utilized to detect block-body radiation originating from a living subject. The processor is configured to run an algorithm to perform digital signal processing on data provided by the radar and the LWIR sensor to generate presence and vitals information for the living subject for communication to the user interface.

19 Claims, 4 Drawing Sheets

(56) References Cited

U.S. PATENT DOCUMENTS

| | | | | |
|---|---|---|---|---|
| 2017/0319114 | A1 | 11/2017 | Kaestle | |
| 2018/0053393 | A1 | 2/2018 | White et al. | |
| 2018/0263502 | A1 | 9/2018 | Lin et al. | |
| 2018/0279885 | A1 | 10/2018 | Bulut | |
| 2019/0000391 | A1 | 1/2019 | De Haan et al. | |
| 2019/0139389 | A1 | 5/2019 | White et al. | |
| 2019/0205655 | A1 | 7/2019 | Matsuoka et al. | |
| 2020/0022628 | A1 | 1/2020 | Tao et al. | |
| 2020/0265602 | A1 | 8/2020 | Ostadabbas et al. | |
| 2020/0268303 | A1* | 8/2020 | Oliva | A61B 5/202 |
| 2020/0345274 | A1 | 11/2020 | Ghoshal et al. | |
| 2021/0181307 | A1 | 6/2021 | Ghaffari Ni et al. | |
| 2021/0274107 | A1* | 9/2021 | Wang | H04N 23/11 |
| 2022/0007950 | A1* | 1/2022 | Lev | A61B 5/7267 |
| 2022/0167850 | A1* | 6/2022 | Schultes | A61B 5/0077 |
| 2023/0377165 | A1* | 11/2023 | Shirai | G01J 5/0859 |

OTHER PUBLICATIONS

International Search Report and Written Opinion for PCT Application PCT/US2022/040235, mailed on Nov. 3, 2022.
International Search Report and Written Opinion for PCT Application PCT/US2022/042515, mailed on Jan. 4, 2023.
Nternational Search Report and Written Opinion for PCT Application PCT/US2022/050257, mailed on Feb. 28, 2023.

* cited by examiner

PRESENCE AND VITALS DETECTION OF LIVING SUBJECT USING LWIR AND RADAR SYSTEMS

CROSS REFERENCE TO RELATED APPLICATION

The Present Application claims priority to U.S. Provisional Patent Application No. 63/226,703, filed on Jul. 28, 2021, which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to infant monitors.

Description of the Related Art

The best sensor for no contact (no wires or wearables) detecting vitals of a living subject is radar because of its sensitivity and ability to permeate materials such as blankets and clothing. Radar has its own set of problems, however, such as susceptibility to RF reflections, spatial sensitivity limited to aimed antennas which are at least partially sensitive in 4π steradians, and low spatial resolution of static objects.

The best sensor for detecting presence of a warm-blooded living subject is a LWIR camera which is able to detect blackbody radiation emitted by the target. This sensor, however, is not ideal for detecting vital signs due to its low range resolution and inability to detect motion perpendicular to the sensor.

The current market is provided only products which rely heavily on visible-range camera information to detect presence, and also for detecting vitals. These systems are compute-heavy, unreliable and easily fooled, are prone to error in dynamic lighting scenarios, and lack the sensitivity to achieve highly accurate vitals detection.

Additionally, a camera based solution has historically become a privacy pain-point for privacy-minded consumers. Due to the compute-heavy nature of these systems, digital processing is often computed in the cloud which can require sending and often storing personally identifiable information on a remote server.

Radar has the sensitivity to detect vitals but presence detection of still or small objects can yield results with low confidence. This is due to the radar's inability to select targets spatially due to the 4π sr sensitivity of an antenna and its susceptibility to multipath and other interference. LWIR is able to detect presence with high confidence but does not have the resolution for vitals detection.

BRIEF SUMMARY OF THE INVENTION

The best way to mitigate these problems is via the inclusion of a LWIR detector which is able to detect black body radiation emitted by the living subject within the detector's fixed and restricted field of view. A LWIR detector is not fooled by RF reflections, is not partially sensitive outside of its designed field of view, and is able to observe blackbody radiation emissions even of static objects.

A radar is orders of magnitude more sensitive for detecting vitals compared to a camera, and LWIR typically has superior discrimination performance for detecting presence of living targets, compared to traditional visible-range image-based solutions.

Additionally, both these sensors are completely immune to dynamic visible-spectrum lighting conditions. Additionally, the compute requirement is significantly lower, to the point where designing a local processing system is trivial.

Because local processing is trivial, transmission of personally identifiable data (which this system does not need to measure or collect) is not sent to a remote server.

Using both sensors, the present invention obtains presence detection and vitals detection with high confidence.

The present invention is a system for using a single pixel or imaging long-wave infrared (LW IR, such as a PIR sensor) "thermal camera" and a radar (single or multichannel, CW, FMCW, PD, etc) for detecting presence and vital signs of a warm-blooded living target.

Additionally, this solution works without the use of a visible camera.

Additionally, visible-spectrum image and video processing for presence and vitals detection is orders of magnitude more compute-heavy compared to low resolution LWIR and radar processing.

Therefore, this solution does not necessitate sending any data to a remote server for computation.

One aspect of the present invention is a system for presence and vitals detection of a living subject. The system comprises a passive long wave infrared ("LWIR") sensor, a radar, a processor and a user interface. The LWIR sensor is utilized to detect block-body radiation originating from a living subject. The radar emits a radiofrequency at a specific frequency, and detects the frequency change of reflections of a plurality of targets which have subtle movements caused by the respiration and/or ballistocardiography from the living subject. The processor is configured to run an algorithm to perform digital signal processing on data provided by the radar and the LWIR sensor to generate presence and vitals information for the living subject for communication to the user interface.

Another aspect of the present invention is a method for presence and vitals detection of a living subject. The method includes detecting at a LWIR sensor of a monitoring device block-body radiation originating from a living subject. The method also includes emitting from a radar of the monitoring device a radiofrequency at a specific frequency, and detecting the frequency change of reflections of a plurality of targets which have subtle movements caused by the respiration and/or ballistocardiography from the living subject. The method also includes receiving at a processor of the monitoring device the data from the radar and the LWIR sensor. The method also includes running on the processor an algorithm to perform digital signal processing on the data provided by the radar and the LWIR sensor to generate presence and vitals information for the living subject. The method also includes communicating from a first communication module of the monitoring device the presence and vitals information for the living subject to a second communication module of an interface device. The method also includes presenting on a user interface module of the interface device the presence and vitals information for the living subject.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

The present invention is a system which consists of a LWIR camera or detector bore-sighted with a radar sensor, and a set of algorithms which operate internally on the system, which determine and transmit presence and vitals information remotely to an observer.

A sensor consists of a passive long wave infrared low-resolution single-detector or imaging sensor is used to detect black body radiation originating from a warm blooded living subject (all of which naturally radiate black body heat). A radar emits RF at a specific frequency, and detects the frequency change of reflections of targets which have subtle movements caused by the respiration and/or ballistocardiography from a living subject.

The field of view of the LWIR sensor and the transmit and receive antenna main lobe sensitivity are roughly collocated, with similar attitude (azimuth and zenith angle). The radar pattern is at least partially sensitive in 4π sr surrounding the radar antenna. An LWIR sensor such as a thermal imager, PIR, or other LWIR detector, is used In order to ensure the spatial sensitivity required to identify the presence of targets, greatly increasing the confidence of a radar system in determining presence of a target.

Figure 1:
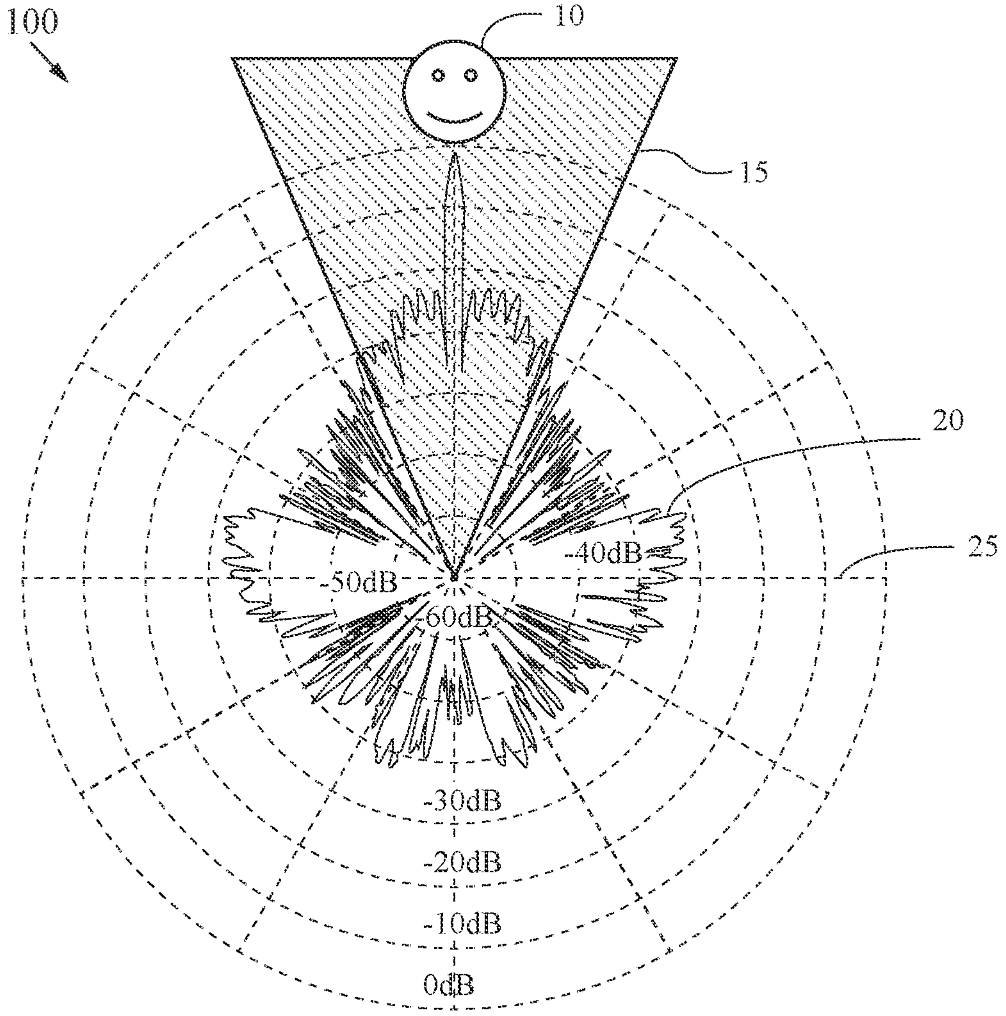
FIG. 1 is an illustration of an antenna pattern.

FIG. 1 is an illustration of an antenna pattern 100 showing the target of interest 10 (the living subject), the LWIR sensor's field of view 15, the radar sensitivity pattern 20, and the Azimuth angle 25.

Digital sensor data from these sensor modules are provided for ingestion by a processor unit, which runs an algorithm internally to perform digital signal processing, feature extraction, decision logic, and preparation for communication with user's module. Data is then transmitted from sensor system communication module to the corresponding user interface system's communication module.

A user interface system consists of a communication module which receives data from its corresponding sensor system. This data is presented to the user via a user interface such as an LED, a display, a speaker, or any other manner of interface.

A long wave infrared detector determines a presence of living subject by detecting black body radiation at 8 μm to 14 μm (8,000 to 14,000 nm) for example. An example of a commercial product is a FLIR Boson 320, Seek Contact.

A radar detects the vitals of living subject by detecting reflected RF. An example of a commercial product is a Xethru X4, Miku Smart Monitor.

A compute module with memory and communication module performs the entirety of the presence and vitals detection within the sensing system.

A user interface system with a communication module receives data and presents information to a user.

A single pixel presence detector performs the following function: monitor sensor output x[n] with sample rate S Hz and store measurement in system memory, a sample rate S could be 1 Hz for example; Apply high pass filter y[n]=x[n]−x[n−k] for time constant k, time constant k could be 10 to represent 10 second delay; and search for y[n]>a & x[n]>b, change threshold a, to detect sudden changes, temperature threshold b, to select temperatures which exceed a threshold.

An imaging sensor presence detector performs the following function: (1) monitor sensor output $X=x_1[i,j]$, $x_2[i,j]$, . . . $x_n[i,j]$ with sample rate S Hz, (a) i, j represent row and column dimension of sensor image and could be (320, 240) for example, (b) sample rate S could be 1 Hz for example; (2) Compute aggregated background value m[n] of image to estimate background temperature, (a) Aggregated background value could be median of all pixels, image pooling, image segmentation, or other; (3) Subtract background from image using bk[n] and segment result, (a) Threshold-and-mask for example: (i) Threshold image based on bk[n] to generate image mask, (j) $y_n[i,j]=x_n[i,j]>bk[n]$ for all i,j in range; (ii) Perform morphological denoise transformation on mask such as erosionl (iii) Sum all values of $y_n$ to calculate mask area a[n]; (iv) If a[n]>k for area threshold k: (1) Apply mask $y_n$ to $x_n$ to generate $z_n$; (2) Sum pixel values of $z_n$ to generate v[n]l; (3) Divide v[n] by a[n] to get mean value of segment m[n] (4) Compare m[n] mean value to temperature threshold b.

An imaging sensor presence detector performs the following function: (1) monitor sensor output $X=x_1[i,j]$, $x_2[i,j]$, $x_n[i,j]$ with sample rate S Hz, (a) i, j represent row and column dimension of sensor image and could be (320, 240) for example, (b) sample rate S could be 1 Hz for example; (2) Compute aggregated background value m[n] of image to estimate background temperature, (a) Aggregated background value could be median of all pixels, image pooling, image segmentation, or other; (3) Subtract background from image using bk[n] and segment result, (a) Threshold-and-mask for example: (i) Threshold image based on bk[n] to generate image mask, (j) $y_n[i,j]=x_n[i,j]>bk[n]$ for all i,j in range; (ii) Perform morphological denoise transformation on mask such as erosionl (iii) Sum all values of $y_n$ to calculate mask area a[n]; (iv) If a[n]>k for area threshold k: (1) Apply mask $y_n$ to $x_n$ to generate $z_n$; (2) Sum pixel values of $z_n$ to generate v[n]l; (3) Divide v[n] by a[n] to get mean value of segment m[n] (4) Compare m[n] mean value to temperature threshold b.

Figure 2:
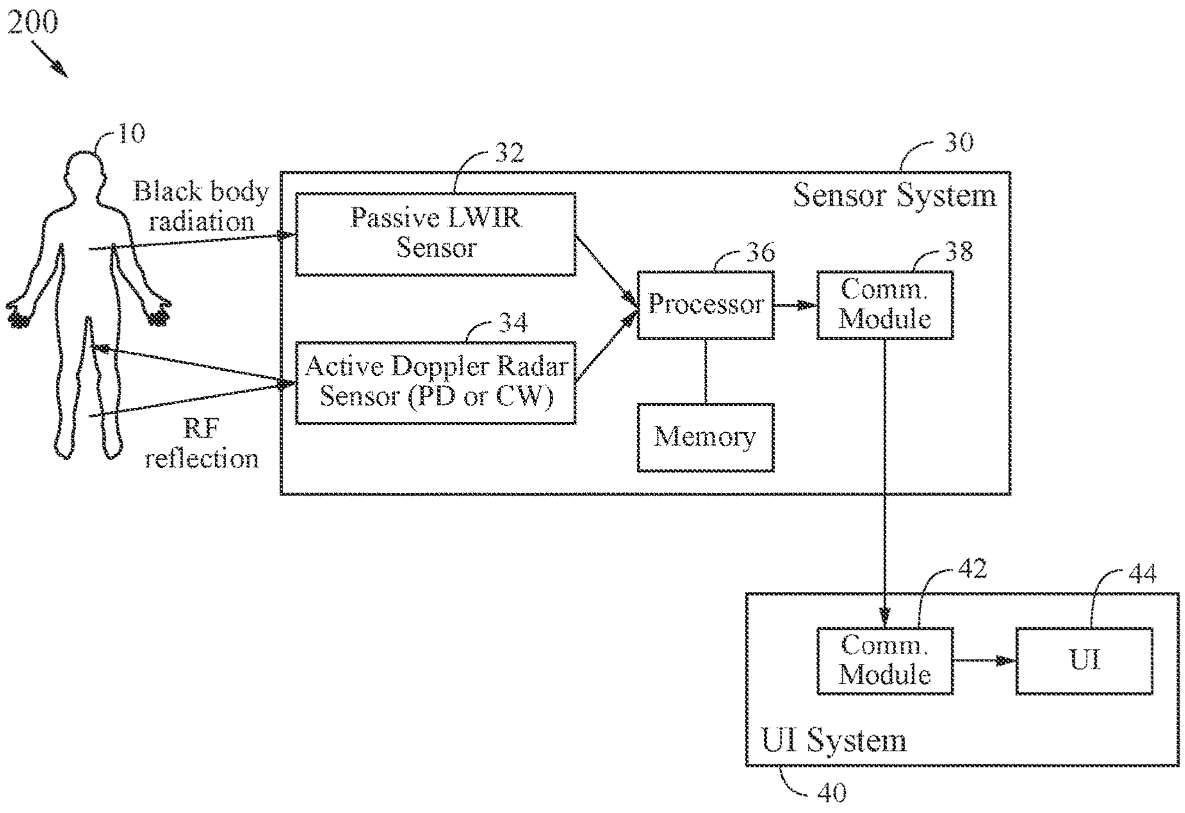
FIG. 2 is a block diagram of one embodiment of a system for presence and vitals detection of a living subject.

FIG. 2 is a block diagram of one embodiment of a system 200 for presence and vitals detection of a living subject 10. As shown in FIG. 2, the system 200 for presence and vitals detection of a living subject 10 comprises a sensor system 30 (monitoring device) and a user interface device 40. The monitoring device 30 comprises a passive long wave infrared low-resolution ("LWIR") sensor 32, a radar 34, a processor 36, and a first communication module 38. The interface device 40 comprises a second communication module 42 and a user interface module 44. The LWIR sensor 32 is utilized to detect block-body radiation originating from a living subject 10. The radar 34 emits a radiofrequency at a specific frequency, and detects the frequency change of reflections of a plurality of targets which have subtle movements caused by the respiration and/or ballistocardiography from the living subject 10. The processor is configured to run an algorithm to perform digital signal processing on data provided by the radar 34 and the LWIR sensor 32 to generate presence and vitals information for the living subject 10 for communication to the interface device 40.

The radar can be a pulsed Doppler radar, FMCW radar, a continuous wave radar, or any other type of radar.

The user interface preferably presents data using a LED, a display or a speaker. The user interface preferably comprises a second communication module for receiving data from a first communication module in communication with the processor.

The memory is preferably configured to store sensor output from the LWIR sensor.

The LWIR sensor is preferably an imaging sensor presence detector or a single pixel presence detector.

The living subject is preferably an infant.

The first communication module and the second communication module preferably operate on a WiFi communication protocol.

Figure 3:
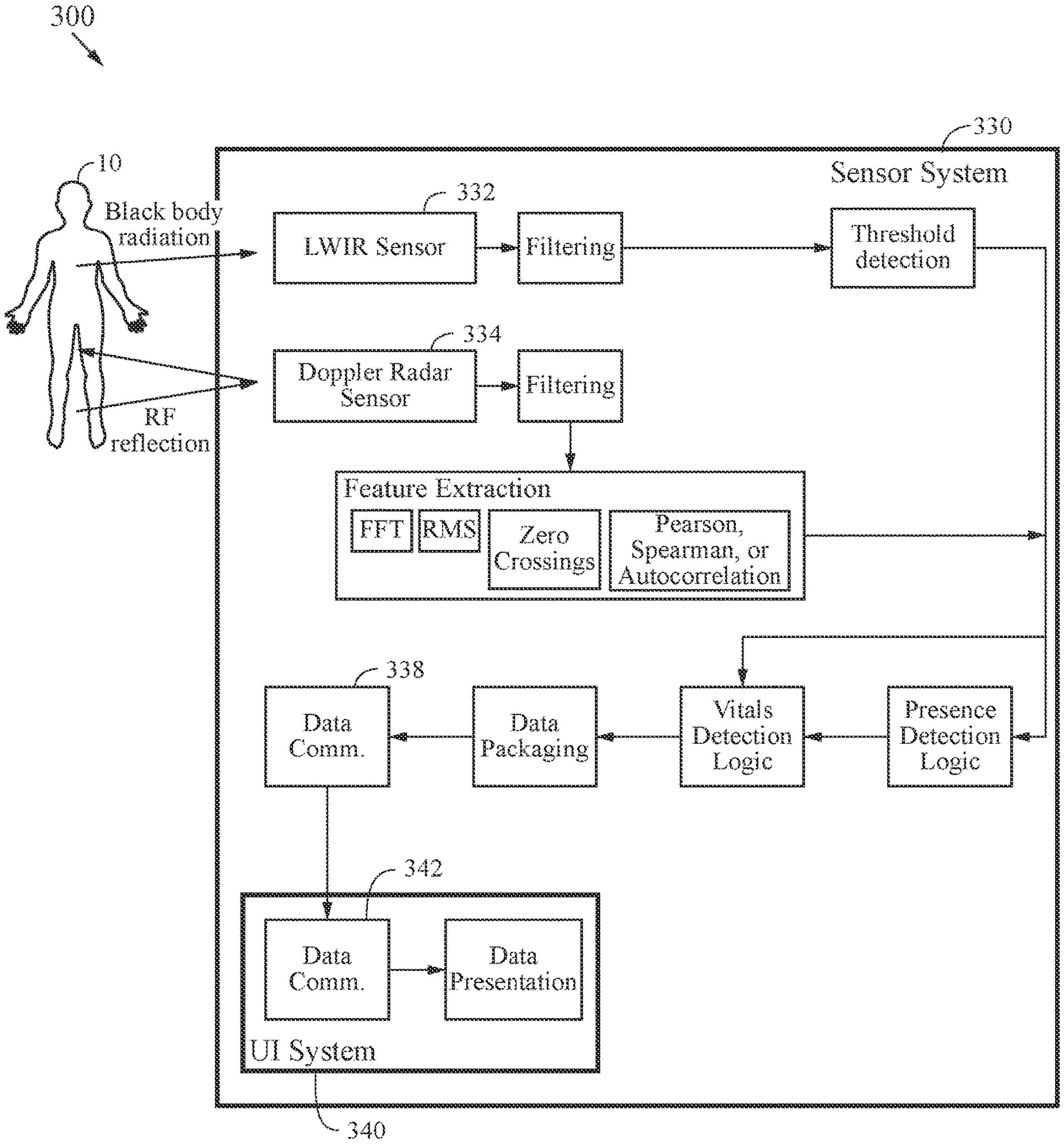
FIG. 3 is a block diagram of a process for presence and vitals detection of a living subject.

FIG. 3 is a block diagram of a process 300 for presence and vitals detection of a living subject. As shown in FIG. 3, a passive long wave infrared low-resolution ("LWIR") sensor 332 determines a presence of living subject 10 by detecting black body radiation. A radar 334 detects the vitals of a living subject 10 by detecting reflected RF. The sensor system 330 processes the data and communicates the data from a communication module 338 to a communication module 342 of the user interface system 340, which displays the data.

Figure 4:
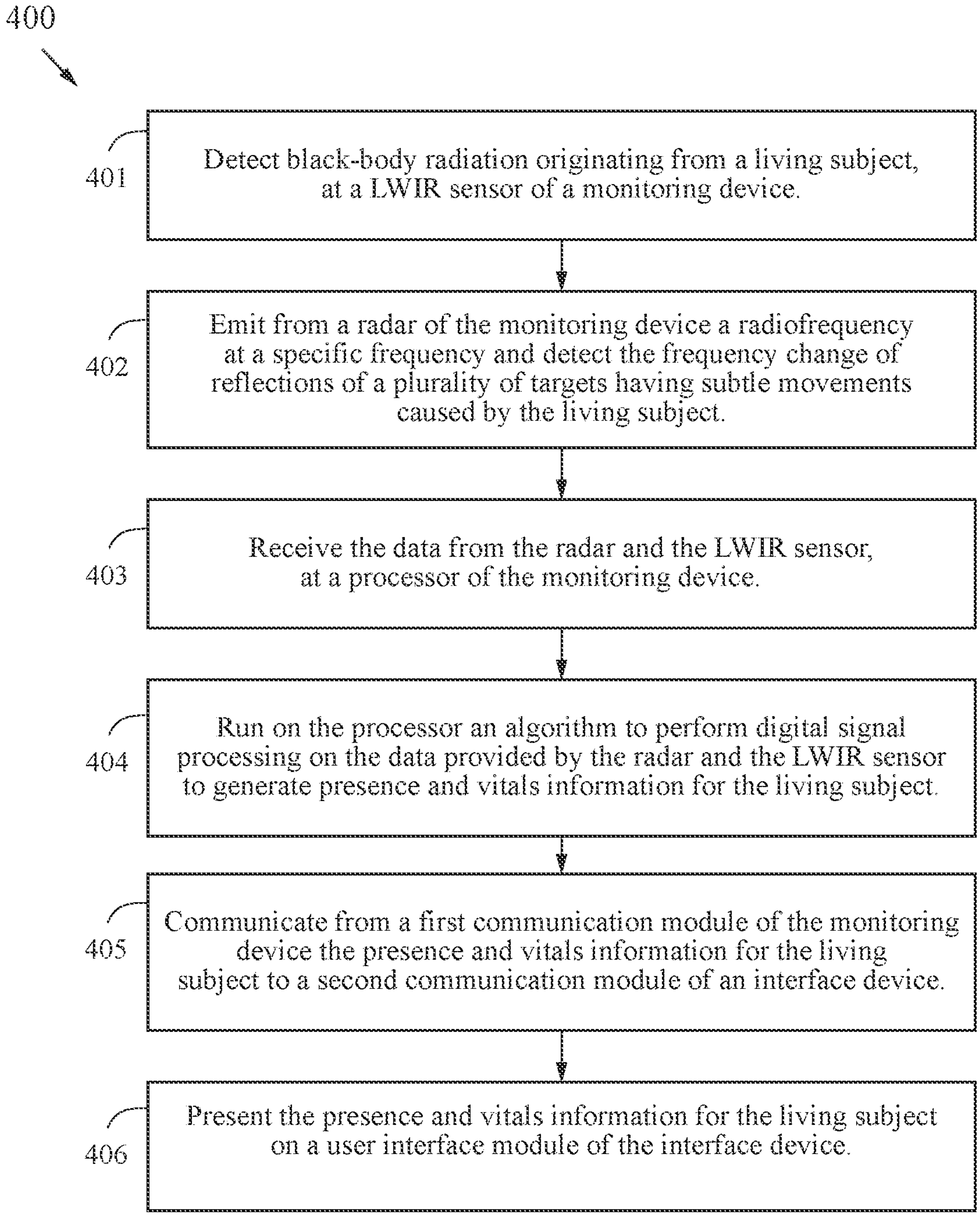
FIG. 4 is a flow chart of a method for presence and vitals detection of a living subject.

FIG. 4 is a flow chart of a method 400 for presence and vitals detection of a living subject. Step 401 starts at a LWIR sensor of a monitoring device, detecting black-body radiation originating from a living subject. Step 402 is emitting from a radar of the monitoring device a radiofrequency at a specific frequency, and detecting the frequency change of reflections of a plurality of targets which have subtle movements caused by the living subject. Step 403 is receiving at a processor of the monitoring device the data from the radar and the LWIR sensor. Step 404 is running on the processor an algorithm to perform digital signal processing on the data provided by the radar and the LWIR sensor to generate presence and vitals information for the living subject. Step 405 is communicating from the monitoring device's communication module 38 the presence and vitals information for the living subject to an interface device's communication module 42. And step 406 is presenting on an interface device the presence and vitals information for the living subject.

White et al., U.S. Pat. No. 10,825,314 for a Baby Monitor, is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A system for presence and vitals detection of a living subject, the system comprising:

a passive long wave infrared low-resolution ("LWIR") sensor;

a Doppler radar;

a processor; and a user interface;

wherein the LWIR sensor is utilized to detect black-body radiation originating from a living subject;

wherein the Doppler radar emits a radiofrequency at a specific frequency, and detects a frequency change of reflections of a plurality of targets which have subtle movements caused by respiration and/or ballistocardiography from the living subject;

wherein the processor is configured to run an algorithm to perform digital signal processing on data provided by the Doppler radar and the LWIR sensor to:

monitor passive LWIR sensor output from the passive LWIR sensor;

determine, for an image captured by the passive LWIR sensor, an aggregated background value of the passive LWIR sensor output, the aggregated background value comprising a median of all pixels of the image to estimate a background temperature;

filter the passive LWIR sensor output based on an image mask derived from the aggregated background value by thresholding the image based on the aggregated background value to segment the image and detect a LWIR-based presence of the living subject in at least one image captured by the LWIR sensor based on a detection of the black-body radiation;

detect, in response to the LWIR-based presence, a Doppler radar-based presence of the living subject based on a detection of the frequency change of reflections;

generate, in response to the LWIR-based presence and the Doppler radar-based presence, vitals information for the living subject based at least in part on the black-body radiation and the frequency change of the reflections; and output the vitals information and the LWIR-based presence and the Doppler radar-based presence for communication to the user interface.

2. The system according to claim 1, wherein the Doppler radar is a pulsed Doppler radar or a continuous wave Doppler radar.

3. The system according to claim 1, wherein the user interface presents data using a light emitting diode (LED) LED, a display or a speaker.

4. The system according to claim 1, wherein the user interface comprises a second communication module for receiving data from a first communication module in communication with the processor.

5. The system according to claim 1, further comprising a memory configured to store sensor output from the passive LWIR sensor.

6. The system according to claim 1, wherein the passive LWIR sensor is an imaging sensor presence detector.

7. The system according to claim 1, wherein the passive LWIR sensor is a single pixel presence detector.

8. A system for presence and vitals detection of a living subject, the system comprising:

a monitoring device comprising a passive longwave infrared low-resolution ("LWIR") sensor, a Doppler radar, a processor, and a first communication module; and an interface device comprising a second communication module and a user interface module;

wherein the passive LWIR sensor is utilized to detect black-body radiation originating from a living subject;

wherein the Doppler radar emits a radiofrequency at a specific frequency, and detects a frequency change of reflections of a plurality of targets which have subtle movements caused by respiration and/or ballistocardiography from the living subject;

wherein the processor is configured to run an algorithm to perform digital signal processing on data provided by the Doppler radar and the LWIR sensor to:

monitor passive LWIR sensor output from the passive LWIR sensor;

determine an aggregate background value of the passive LWIR sensor output the aggregate background value comprising an aggregation of background values of a background of each image captured by the passive LWIR sensor;

filter the passive LWIR sensor output based on an image mask derived from the aggregate background value to detect a LWIR-based presence of the living subject based on a detection of the black-body radiation;

detect, in response to the LWIR-based presence, a Doppler radar-based presence of the living subject based on a detection of the frequency change of reflections;

generate, in response to the LWIR-based presence and the Doppler radar-based presence, vitals information for the living subject based at least in part on the black-body radiation and the frequency change of the reflections; and output the vitals and the LWIR-based presence and the Doppler radar-based presence information for communication to a user interface.

9. The system according to claim 8, wherein the Doppler radar is a pulsed Doppler radar or a continuous wave Doppler radar.

10. The system according to claim 8, wherein the first communication module is configured to transmit data to the second communication module.

11. The system according to claim 8, wherein the monitoring device further comprises a memory configured to store sensor output from the passive LWIR sensor.

12. The system according to claim 8, wherein the passive LWIR sensor is an imaging sensor presence detector or a single pixel presence detector.

13. A method for presence and vitals detection of a living subject, the method comprising:

detecting at a passive long wave infrared low-resolution (LWIR) sensor of a monitoring device black-body radiation originating from a living subject;

emitting from a Doppler radar of the monitoring device a radiofrequency at a specific frequency, and detecting a frequency change of reflections of a plurality of targets which have subtle movements caused by the respiration and/or ballistocardiography from the living subject;

receiving at a processor of the monitoring device the data from the Doppler radar and the passive LWIR sensor;

running on the processor an algorithm to perform digital signal processing on the data provided by the Doppler radar and the LWIR sensor to wherein the processor is configured to run an algorithm to perform digital signal processing on data provided by the Doppler radar and the passive LWIR sensor to:

monitor passive LWIR sensor output from the passive LWIR sensor;

determine, for an image captured by the passive LWIR sensor, an aggregated background value of the passive LWIR sensor output, the aggregated background value comprising a median of all pixels of the image to estimate a background temperature;

filter the passive LWIR sensor output based on an image mask derived from the aggregate background value to detect a LWIR-based presence of the living subject based on a detection of the black-body radiation;

detect, in response to the LWIR-based presence, a Doppler radar-based presence of the living subject based on a detection of the frequency change of reflections;

generate, in response to the LWIR-based presence and the Doppler radar-based presence information, vitals information for the living subject based at least in part on the black-body radiation and the frequency change of the reflections; and output the vitals information and the LWIR-based presence and the Doppler radar-based presence information for communication to the a user interface;

communicating from a first communication module of the monitoring device the presence and vitals information for the living subject to a second communication module of an interface device;

and presenting on a user interface module of the interface device the presence and vitals information for the living subject.

14. The method according to claim 13, wherein the Doppler radar is a pulsed Doppler radar or a continuous wave Doppler radar.

15. The method according to claim 13, wherein the monitoring device further comprises a memory configured to store sensor output from the passive LWIR sensor.

16. The method according to claim 13, wherein the passive LWIR sensor is an imaging sensor presence detector.

17. The method according to claim 13 wherein the passive LWIR sensor is a single pixel presence detector.

18. The method according to claim 13, wherein the living subject is an infant.

19. The method according to claim 13, wherein the first communication module and the second communication module operate on a communication protocol conforming to the WiFi™ standard.

* * * * *